United States Patent [19]

Roth et al.

[11] 4,311,701

[45] Jan. 19, 1982

[54] TREATMENT OF CONVULSIONS WITH TRIAZINES

[76] Inventors: Barbara Roth, 7 Lone Pine Rd., Chapel Hill, N.C. 27514; Alistair A. Miller, 91 Elmshurst Gardens, Tonbridge, Kent; David A. Sawyer, 60 Bourne Vale, Hayes, Kent, both of England

[21] Appl. No.: 177,886

[22] Filed: Aug. 14, 1980

[30] Foreign Application Priority Data

Aug. 16, 1979 [GB] United Kingdom ............... 28641/79

[51] Int. Cl.³ ............................................. A61K 31/53
[52] U.S. Cl. .................................................... 424/249
[58] Field of Search .......................................... 424/249

[56] References Cited

U.S. PATENT DOCUMENTS 3,637,688  1/1972  Rees et al. .......................... 424/249

OTHER PUBLICATIONS

Rees et al., J. Med. Chem. 15, p. 859 (1972).

Primary Examiner—Stanley J. Friedman
Attorney, Agent, or Firm—Donald Brown

[57] ABSTRACT

The medical use of compounds of the formula (III):

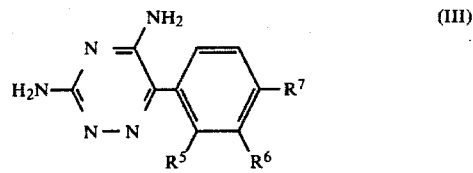

or pharmaceutically acceptable and addition salts thereof, wherein $R^6$ is a hydrogen atom, $R^5$ is a chlorine atom and $R^7$ is a hydrogen or chlorine atom or $R^7$ is a chlorine atom, $R^5$ is a hydrogen atom and $R^6$ is a chlorine atom, particularly for the treatment of CNS disorders, is disclosed. Solid pharmaceutical compositions are also described.

8 Claims, No Drawings

TREATMENT OF CONVULSIONS WITH TRIAZINES

The present invention relates to a group of compounds which are useful in the treatment of CNS disorders, such as epilepsy, to certain pharmaceutical compositions containing them, and to methods for their preparation.

U.K. Pat. No. 759,014 discloses compounds of the formula (I):

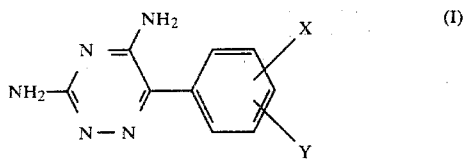

wherein X and Y are hydrogen and halogen atoms, as having activity against bacterial and malarial infections in animals. This patent specifically discloses those compounds wherein X and Y are both hydrogen atoms, wherein X is a hydrogen atom and Y is a 4-chloro atom and wherein X is a 4-chloro atom and Y is a 2-chloro and 3-chloro atom respectively.

Rees et al (J. Med. Chemo., 1972, 15, 859), have shown that these compounds, and in particular the 4-chlorophenyl, and the 3,4-dichlorophenyl compounds are active against the malaria organism *P. berghei* in mice. However, these compounds were also shown to be toxic and were not investigated further because of their low therapeutic ratio. The 2,4-dichlorophenyl compound had only slight antimalarial activity. The therapeutic ratios of the compounds were such as to prevent their use in human medicine for the treatment or prophylaxis of malaria and they were not progressed further.

U.S. Pat. No. 3,637,688 discloses compounds of the formula (II):

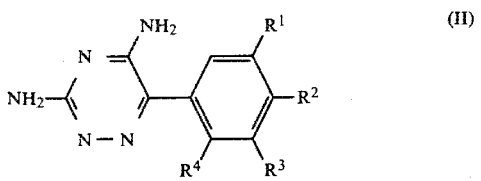

wherein $R^1$ is hydrogen or fluorine, and $R^2$, $R^3$ and $R^4$ are hydrogen, fluorine or trifluoromethyl provided that at least one of $R^1$, $R^2$, $R^3$ and $R^4$ is fluorine or trifluoromethyl, as being useful in the treatment of malaria. In the Rees article referred to above, the 4-trifluoromethylphenyl compound was claimed to be less toxic than the chlorophenyl compounds whilst still being active against malaria. The other fluoro and trifluoromethyl compounds referred to in the article were substantially less active than the 4-trifluoromethylphenyl compound.

Rosenberg and Bottiroli (Proc. Soc. exp, Biol., 1964 115, 410, described a series of tests in which three antimalarial agents, quinacrine, chloroquine and hydroxychloroquine, were tested as anticonvulsants. Only hydroxychloroquine possessed a favourable activity profile.

It has now been discovered that a group of 3,5-diamino-6-(substituted phenyl)-1,2,4-triazines are active in the treatment of CNS disorders, such as psychiatric and neurological disorders, and are particularly useful as anticonvulsants, for example in the treatment of epilepsy. Furthermore, these triazines are nondepressant and therefore are advantageous over depressant antiepileptics, such as phenobarbitone.

Accordingly, the present invention provides a compound of the formula (III):

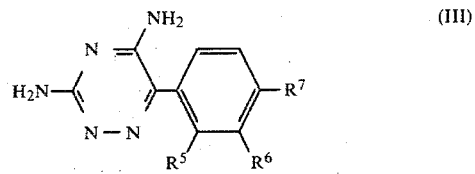

or an acid addition salt thereof, wherein either $R^6$ is a hydrogen atom, $R^5$ is a chlorine atom and $R^7$ is a hydrogen or chlorine atom or $R^7$ is a chlorine atom, $R^5$ is a hydrogen atom and $R^6$ is a chlorine atom, for use in medicine, for example for the treatment of CNS disorders, such as epilepsy.

Preferred compounds for the treatment of epilepsy are: 3,5-diamino-6-(2,4-dichlorophenyl)-1,2,4-triazine and 3,5-diamino-6-(2-chlorophenyl)-1,2,4-triazine or acid addition salts thereof.

Suitable acid addition salts of the compounds of formula (III) include those formed with both organic and inorganic acids. Such acid addition salts will normally be pharmaceutically acceptable. Thus, preferred salts include those formed from hydrochloric, sulphuric, citric, tartaric, phosphoric, lactic, pyruvic, acetic, succinic, oxalic, fumaric, maleic, oxaloacetic acids, methanesulphoric, P-toluenesulphoric and benzenesulphoric acids.

It has been found that certain novel solid pharmaceutical formulations of compounds of the formula (III) are also advantageous in the treatment of CNS disorders in humans.

Accordingly the present invention provides a solid pharmaceutical formulation provided in discrete units, such as a tablet which contains an amount of a compound of the formula (III), as hereinbefore defined, which is effective at such dosage or a multiple of the same, for instance such units contain 25 mg to 500 mg., usually around 50 mg to 250 mg.

Other solid formulations include fine powders or granules which may contain diluting, dispersing and/or surface active agents and are formulated in suitable dosage forms in capsules or sachets.

The solid formulations may contain and preferably will contain standard, pharmaceutically acceptable carriers for the purpose of administering the medicaments. Inert ingredients which may suitably be incorporated in the formulations of the present invention include lactose, starch, calcium phosphate, talc, magnesium stearate and the like.

The formulations will be prepared by techniques well known to those skilled in the art. Thus, when a pharmaceutically acceptable carrier is present the solid formulations will be prepared by the admixture of a compound of the formula (III) with the pharmaceutically acceptably carrier. Conventional pharmaceutical excipients may be admixed as required.

The present invention provides a method of treatment of convulsions, particularly epilepsy, in mammals, for example humans, by the administration of a non-toxic anticonvulsant effective amount of a compound of the formula (III), or a pharmaceutically acceptable salt, or a composition, as hereinbefore defined.

As indicated above, the compounds of the formula (III) are generally useful in treating such disorders by oral administration.

The compounds of the formula (III) are normally administered at a dose of from 1 mg/kg to 30 mg/kg per day. The dose range for adult humans is generally from 20 mg. to 2400 mg./day and preferably 350 to 1200 mg/day. Due to the fact that the compounds of the formula (III) are extremely long acting, it may often be advantageous to administer an initial dose of 70 to 2400 mg. the first day and then a lower dose of 20 to 1200 mg. on subsequent days.

The compounds of the formula (III) may be prepared by the method described in U.K. Pat. No. 759,014 and U.S. Pat. No. 3,637,688.

The anti-convulsant activity of the three compounds of the present invention was determined by a standard maximal electroshock test, that described by L. A. Woodbury and V. D. Devenport, Arch. Int. Pharmacodyn., 1952, 92, 97.

|  | ED$_{50}$ mg/kg P.O. mice |
|---|---|
| 3,5-diamino-6-(2-chlorophenyl)-1,2,4-triazine | 10.5 |
| 3,5-diamino-6-(2,4-dichloro-phenyl)-1,2,4-triazine | 18.7 |
| 3,5-diamino-6-(3,4-dichloro-phenyl)-1,2,4-triazine. | 17.2 |

The LD$_{50}$ (acute) of 3,5-diamino-6-(2-chlorophenyl)-1,2,4-triazine is approximately 1225 mg/kg p.o. in mice.

| Tablet Example | | |
|---|---|---|
| 3,5-Diamino-6-(2,4-dichoro-phenyl)-1,2,4-triazine | 150mg | |
| Lactose | 200mg | |
| Maize Starch | 50mg | contents per tablet |
| Polyvinylpyrrolidone | 4mg | |

| Tablet Example | |
|---|---|
| Magnesium Stearate | 4mg |

The drug was mixed with the lactose and starch and granulated with a solution of the polyvinylpyrrolidone in water. The resultant granules were dried, mixed with magnesium stearate and compressed to give tablets of average weight 408 mg.

We claim:

1. A method of treatment of convulsions in a human comprising the oral administration to a human of a non-toxic anticonvulsant effective amount of a compound of the formula (III):

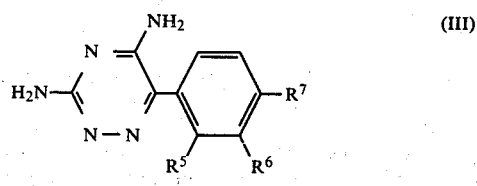

or a pharmaceutically acceptable acid addition salt thereof, wherein $R^6$ is a hydrogen atom, $R^5$ is a chlorine atom and $R^7$ is a hydrogen or chlorine atom or $R^7$ is a chlorine atom, $R^5$ is a hydrogen atom and $R^6$ is a chlorine atom.

2. A method of treatment of convulsions according to claim 1 wherein the compound of the formula (III) is 3,5-diamino-6-(2,4-dichlorophenyl)-1,2,4-triazine or a pharmaceutically acceptable acid addition salt thereof.

3. A method of treatment of convulsions according to claim 1 wherein the compound of the formula (III) is 3,5-diamino-6-(2-chlorophenyl)-1,2,4-triazine or a pharmaceutically acceptable salt thereof.

4. The method of claims 1, 2 or 3 in which the compound or salt is administered in unit dose form together with a pharmaceutically acceptable carrier.

5. The method of claim 1 in which the compound or salt is administered in the form of a tablet.

6. The method of claim 2 in which the compound or salt is administered in the form of a tablet.

7. The method of claim 3 in which the compound or salt is administered in the form of a tablet.

8. The method of claim 1, 2 or 3 in which the compound or salt is administered in a solid form.